United States Patent
Daubersies

(10) Patent No.: US 11,771,629 B2
(45) Date of Patent: *Oct. 3, 2023

(54) PROCESS FOR THE ELONGATION AND/OR DENSIFICATION OF FIBERS

(71) Applicant: L'OREAL, Paris (FR)

(72) Inventor: Laure Daubersies, Chevilly Larue (FR)

(73) Assignee: L'OREAL, Paris (FR)

( * ) Notice: Subject to any disclaimer, the term of this patent is extended or adjusted under 35 U.S.C. 154(b) by 861 days.

This patent is subject to a terminal disclaimer.

(21) Appl. No.: 16/310,998

(22) PCT Filed: Jun. 22, 2017

(86) PCT No.: PCT/EP2017/065451
§ 371 (c)(1),
(2) Date: Dec. 18, 2018

(87) PCT Pub. No.: WO2017/220743
PCT Pub. Date: Dec. 28, 2017

(65) Prior Publication Data
US 2020/0261335 A1    Aug. 20, 2020

(30) Foreign Application Priority Data

Jun. 23, 2016 (FR) ...................... 1655881

(51) Int. Cl.
| | |
|---|---|
| *A61K 8/31* | (2006.01) |
| *A61K 8/02* | (2006.01) |
| *A61K 8/81* | (2006.01) |
| *A61Q 1/10* | (2006.01) |

(52) U.S. Cl.
CPC .............. *A61K 8/31* (2013.01); *A61K 8/0241* (2013.01); *A61K 8/8152* (2013.01); *A61Q 1/10* (2013.01); *A61K 2800/614* (2013.01); *A61K 2800/654* (2013.01)

(58) Field of Classification Search
None
See application file for complete search history.

(56) References Cited

U.S. PATENT DOCUMENTS

| | | |
|---|---|---|
| 2004/0120906 A1 | 6/2004 | Toumi et al. |
| 2006/0093568 A1 | 5/2006 | Blin et al. |
| 2006/0099164 A1 | 5/2006 | De La Poterie et al. |
| 2006/0115444 A1 | 6/2006 | Blin et al. |
| 2006/0127334 A1 | 6/2006 | Ferrari et al. |
| 2006/0134032 A1 | 6/2006 | Ilekti et al. |
| 2006/0134044 A1 | 6/2006 | Blin et al. |
| 2006/0134051 A1 | 6/2006 | Blin et al. |
| 2006/0147402 A1 | 7/2006 | Blin et al. |
| 2006/0147403 A1 | 7/2006 | Ferrari et al. |
| 2016/0317423 A1 | 11/2016 | Portal et al. |
| 2017/0360657 A1* | 12/2017 | Daubersies .......... A61K 8/8164 |

FOREIGN PATENT DOCUMENTS

| | | |
|---|---|---|
| EP | 1 552 806 A1 | 7/2005 |
| FR | 3 014 875 A1 | 6/2015 |
| FR | 3 029 786 A1 | 6/2016 |
| JP | 2005-225867 A | 8/2005 |
| WO | WO 2015/091513 A1 | 6/2015 |

OTHER PUBLICATIONS

Japanese Office Action dated Jan. 6, 2020 in Patent Application No. 2018-567054 (with English translation), 6 pages.
International Search Report dated Sep. 19, 2017 in PCT/EP2017/065451 filed Jun. 22, 2017.
French Preliminary Search Report dated Oct. 26, 2016 in French Application 16 55881 filed on Jun. 23, 2016 (with English Translation of Categories of Cited Documents).

* cited by examiner

*Primary Examiner* — David J Blanchard
*Assistant Examiner* — Sarah J Chickos
(74) *Attorney, Agent, or Firm* — Oblon, McClelland, Maier & Neustadt, L.L.P.

(57) ABSTRACT

The present invention relates to a process for the elongation and/or densification of fibers, on a keratin material, characterized in that it employs a composition, especially a cosmetic composition, in particular a makeup composition, comprising at least: —one volatile hydrocarbon-based oil, —particles of at least one polymer surface-stabilized with a stabilizer, and —a hydrophobic film-forming polymer, chosen from hydrocarbon-based block copolymers, hydrocarbon-based resins, and mixtures thereof.

17 Claims, No Drawings

PROCESS FOR THE ELONGATION AND/OR DENSIFICATION OF FIBERS

The present invention relates to the field of making up keratin materials and/or keratin fibers, and aims to propose a process for the elongation and/or densification of fibers, on a keratin material, in particular on the skin and/or on the keratin fibers, more particularly on the keratin fibers, employing an adhesive cosmetic composition.

The term "keratin materials" preferably means human keratin materials, especially keratin fibers.

The term "keratin fibers" in particular means the eyelashes and/or the eyebrows, and preferably the eyelashes. For the purposes of the present invention, this term "keratin fibers" also extends to synthetic false eyelashes.

The present invention proves to be most particularly advantageous for making up keratin materials.

Generally, mascara users seek to make their eyelashes more visible by elongation and/or densification.

An alternative to mascara compositions consists in adhering "false eyelashes" to the eyelid, or in adhering artificial fibers to the existing keratin fibers.

This provides a real transformation of the entirety of the keratin fibers, but requires professional handling, which limits the daily use thereof.

Indeed, these articles for enhancement are generally held on the keratin materials by means of adhesive compositions suited to this use.

One difficulty encountered is that of finding a composition with good adhesion, which can be applied to the skin or to the eyelash, while being risk-free from a toxicology perspective (unlike cyanoacrylate adhesives).

The aim of the present invention is therefore to provide a process for the elongation and/or densification of fibers, on a keratin material, employing a composition without toxicology risks, especially a cosmetic composition, having sufficient fluidity to obtain a good spread of the composition, while having a good adhesive effect.

Another aim of the present invention is to provide a process for the adhesion of "false eyelashes" to the eyelid, or of artificial fibers to the existing keratin fibers employing a composition without toxicology risks, especially a cosmetic composition, having sufficient fluidity to obtain a good spread of the composition, while having a good adhesive effect.

Thus, according to a first aspect thereof, the present invention relates to a process for the elongation and/or densification of fibers, on a keratin material, in particular on the skin and/or on the keratin fibers, more particularly on the keratin fibers, preferably on the eyelashes or the eyebrows, and more preferentially on the eyelashes, characterized in that it employs a composition, especially a cosmetic composition, in particular a makeup composition, comprising at least:
  one volatile hydrocarbon-based oil,
  particles of at least one polymer that is surface-stabilized with a stabilizer, the polymer of the particles being a $C_1$-$C_4$ alkyl (meth)acrylate polymer; the stabilizer being an isobornyl (meth)acrylate polymer chosen from isobornyl (meth)acrylate homopolymer and statistical copolymers of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than 4; and
  a hydrophobic film-forming polymer, preferably chosen from hydrocarbon-based block copolymers, hydrocarbon-based resins, and mixtures thereof.

According to an advantageous variant, said particles are in dispersion in a non-aqueous medium containing at least the volatile hydrocarbon-based oil.

Indeed, contrary to all expectations, and as demonstrated in the experimental section below, the inventors have found that the presence of at least one hydrocarbon-based oil as defined below, of at least specific particles of at least one stabilized polymer as defined below, and of at least one specific hydrophobic film-forming polymer as defined below, makes it possible to achieve a formulation with the expected properties in terms of fluidity, and advantageously making it possible to obtain a good spread of the composition, while achieving enhanced, longer-lasting adhesion.

Indeed, compositions according to the present invention have a very good adhesive effect, and allow the adhesion of "false eyelashes" to the eyelid, or of artificial fibers to the existing keratin fibers, without toxicology risks.

FR 3 014 875 describes particles such as those considered in the present invention. However, the compositions illustrated in this document does not contain hydrophobic film-forming polymers and are not indicated and not adapted as adhesive compositions for the adhesion of "false eyelashes" to the eyelid, or of artificial fibers to the existing keratin fibers.

Hydrophobic Film-Forming Polymers

As stated previously, a composition of the process according to the invention comprises at least one hydrophobic film-forming polymer.

A hydrophobic film-forming polymer that is suitable for the invention is preferably chosen from hydrocarbon-based block copolymers, hydrocarbon-based resins, and mixtures thereof.

In the present patent application, the term "film-forming polymer" means a polymer that is capable, by itself or in the presence of an auxiliary film-forming agent, of forming a macroscopically continuous deposit, and preferably a cohesive deposit, and even better still a deposit whose cohesion and mechanical properties are such that said deposit can be isolated and manipulated individually, for example when said deposit is prepared by pouring onto a non-stick surface such as a Teflon-coated or silicone-coated surface.

The term "hydrophobic" or "water-insoluble" polymer means that the polymer is not soluble in water, according to the definition below.

The term "water-soluble polymer" means that the polymer dissolves in water or in a 50/50 by volume mixture of water and ethanol, or alternatively a mixture of water and isopropanol, without modification of the pH, at a solids content of 5% by weight, at room temperature (25° C., 1 atm.). The polymer is considered to be soluble if it does not form a precipitate or agglomerate that is visible to the naked eye when it is placed in solution, and therefore gives a clear solution.

1. Hydrocarbon-Based Block Copolymers

According to one embodiment, the composition of the process according to the present invention may comprise at least one hydrocarbon-based block copolymer.

The term "block" polymer means a polymer comprising at least 2 separate blocks and preferably at least 3 separate blocks.

The hydrocarbon-based block copolymers that are suitable for the invention are preferably soluble or dispersible in the oily phase.

The hydrocarbon-based block copolymer may especially be a diblock copolymer.

Such hydrocarbon-based block copolymers are described in patent application US-A-2002/005562 and in patent U.S. Pat. No. 5,221,534.

The copolymer may have at least one block whose glass transition temperature is preferably less than 20° C., preferably less than or equal to 0° C., preferably less than or equal to −20° C. and more preferably less than or equal to −40° C. The glass transition temperature of said block may be between −150° C. and 20° C. and especially between −100° C. and 0° C.

The hydrocarbon-based block copolymer present in the composition of the process according to the invention may be an amorphous copolymer formed by polymerization of an olefin. The olefin may especially be an elastomeric ethylenically unsaturated monomer.

The term "amorphous polymer" means a polymer that does not have a crystalline form.

Examples of olefins that may be mentioned include ethylenic carbide monomers, especially containing one or two ethylenic unsaturations and having from 2 to 5 carbon atoms, such as ethylene, propylene, butadiene, isoprene or pentadiene.

Advantageously, the hydrocarbon-based block copolymer is an amorphous block copolymer of styrene and olefin.

Block copolymers comprising at least one styrene block and at least one block comprising units chosen from butadiene, ethylene, propylene, butylene and isoprene or one of the mixtures thereof are especially preferred.

According to one preferred embodiment, the hydrocarbon-based block copolymer is hydrogenated to reduce the residual ethylenic unsaturations after the polymerization of the monomers.

In particular, the hydrocarbon-based block copolymer is an optionally hydrogenated copolymer, containing styrene blocks and ethylene/$C_3$-$C_4$ alkylene blocks.

According to one preferred embodiment, the composition according to the invention comprises at least one diblock copolymer, which is preferably hydrogenated, preferably chosen from styrene-ethylene/propylene copolymers, styrene-ethylene/butadiene copolymers and styrene-ethylene/butylene copolymers. Diblock polymers are especially sold under the name Kraton® G1701E by the company Kraton Polymers.

A diblock copolymer such as those described above, in particular a styrene-ethylene/propylene diblock copolymer, is advantageously used as hydrocarbon-based block copolymer.

In particular, the hydrocarbon-based block copolymer(s) are present in the composition in a content ranging from 0% to 18% by weight relative to the total weight of the composition, preferably ranging from 1% to 16% by weight and even more advantageously from 2% to 16% by weight relative to the total weight of the composition.

2. Hydrocarbon-Based Resins:

As stated previously, the claimed compositions may comprise at least one hydrocarbon-based resin, especially as detailed hereinbelow.

The hydrocarbon-based resins are preferably chosen from low molecular weight polymers that may be classified, according to the type of monomer they comprise, as:

indene hydrocarbon-based resins, preferably such as resins derived from the polymerization in major proportion of indene monomer and in minor proportion of a monomer chosen from styrene, methylindene and methylstyrene, and mixtures thereof. These resins may optionally be hydrogenated. These resins may have a molecular weight ranging from 290 to 1,150 g/mol;

Examples of indene resins that may be mentioned include those sold under the reference Escorez 7105 by the company Exxon Chem., Nevchem 100 and Nevex 100 by the company Neville Chem., Norsolene S105 by the company Sartomer, Picco 6100 by the company Hercules and Resinall by the company Resinall Corp., or the hydrogenated indene/methylstyrene/styrene copolymers sold under the name "Regalite" by the company Eastman Chemical, in particular Regalite R 1100, Regalite R 1090, Regalite R-7100, Regalite R1010 Hydrocarbon Resin and Regalite R1125 Hydrocarbon Resin;

aliphatic pentanediene resins such as those derived from the majority polymerization of the 1,3-pentanediene (trans- or cis-piperylene) monomer and of minor monomer(s) chosen from isoprene, butene, 2-methyl-2-butene, pentene and 1,4-pentanediene, and mixtures thereof; These resins may have a molecular weight ranging from 1,000 to 2,500 g/mol;

Such 1,3-pentanediene resins are sold, for example, under the references Piccotac 95 by the company Eastman Chemical, Escorez 1304 by the company Exxon Chemicals, Nevtac 100 by the company Neville Chem. or Wingtack 95 by the company Goodyear;

mixed resins of pentanediene and of indene, which are derived from the polymerization of a mixture of pentanediene and indene monomers such as those described above, for instance the resins sold under the reference Escorez 2101 by the company Exxon Chemicals, Nevpene 9500 by the company Neville Chem., Hercotac 1148 by the company Hercules, Norsolene A 100 by the company Sartomer, and Wingtack 86, Wingtack Extra and Wingtack Plus by the company Goodyear;

diene resins of cyclopentanediene dimers such as those derived from the polymerization of a first monomer chosen from indene and styrene, and of a second monomer chosen from cyclopentanediene dimers such as dicyclopentanediene, methyldicyclopentanediene and other pentanediene dimers, and mixtures thereof. These resins generally have a molecular weight ranging from 500 to 800 g/mol, for instance those sold under the reference Betaprene BR 100 by the company Arizona Chemical Co., Neville LX-685-125 and Neville LX-1000 by the company Neville Chem., Piccodiene 2215 by the company Hercules, Petro-Rez 200 by the company Lawter or Resinall 760 by the company Resinall Corp.;

diene resins of isoprene dimers such as terpenic resins derived from the polymerization of at least one monomer chosen from α-pinene, limonene, and mixtures thereof. These resins may have a molecular weight ranging from 300 to 2000 g/mol. Such resins are sold, for example, under the names Piccolyte A115 and 5125 by the company Hercules or Zonarez 7100 or Zonatac 105 Lite by the company Arizona Chem.

According to a preferred embodiment, the hydrocarbon-based resin is chosen from hydrocarbon-based resins that are solid at room temperature (20° C.).

According to a preferred embodiment, the hydrocarbon-based resin is chosen from indene hydrocarbon-based resins, aliphatic pentadiene resins, mixed resins of pentanediene and of indene, diene resins of cyclopentanediene dimers and diene resins of isoprene dimers, and mixtures thereof.

Preferably, the composition comprises at least one compound chosen from hydrocarbon-based resins as described previously, especially from indene hydrocarbon-based resins and aliphatic pentadiene resins, and mixtures thereof.

According to one preferred embodiment, the hydrocarbon-based resin is chosen from indene hydrocarbon-based resins.

According to a preferred embodiment, the resin is chosen from hydrogenated indene/methylstyrene/styrene copolymers.

In particular, use may be made of hydrogenated indene/methylstyrene styrene copolymers, such as those sold under the name Regalite by the company Eastman Chemical, such as Regalite R 1100 CG Hydrocarbon Resin, Regalite R 1100, Regalite R 1090, Regalite R-7100, Regalite R1010 Hydrocarbon Resin and Regalite R1125 Hydrocarbon Resin.

A composition according to the invention may comprise from 5% to 50% by weight, preferably from 5% to 45% by weight and even more preferentially from 8% to 40% by weight of hydrocarbon-based resin(s) relative to the total weight of the composition.

In a process according to the invention, the hydrocarbon-based resin is preferably chosen from indene hydrocarbon-based resins, aliphatic pentadiene resins, mixed resins of pentanediene and of indene, diene resins of cyclopentanediene dimers, diene resins of isoprene dimers and mixtures thereof, preferably from indene hydrocarbon-based resins, pentadiene aliphatic resins, and mixtures thereof, and more preferentially from indene hydrocarbon-based resins.

In particular, the hydrocarbon-based resin(s) is(are) present in a content ranging from 0% to 60% by weight, preferably from 5% to 55% by weight and even more preferentially from 8% to 55% by weight relative to the total weight of the composition.

The hydrocarbon-based resin(s) is(are) preferably present in a content ranging from 0% to 70% by weight, preferably from 5% to 55% by weight and even more preferentially from 10% to 40% by weight relative to the total weight of the composition.

According to a particularly preferred embodiment, the composition of the process according to the invention comprises a styrene-ethylene/propylene diblock copolymer and an indene hydrocarbon-based resin.

According to the invention, the hydrophobic film-forming polymer(s) are different from the polymers of the particles. Therefore, the compositions according to the invention comprise both polymer particles that are surface-stabilized with a stabilizer and at least one hydrophobic film-forming polymer.

Hydrocarbon-Based Oil

The composition of the process according to the invention comprises a hydrocarbon-based oil.

This oil may be volatile (vapor pressure greater than or equal to 0.13 Pa measured at 25° C.) or nonvolatile (vapor pressure less than 0.13 Pa measured at 25° C.).

A composition according to the invention comprises at least one volatile hydrocarbon-based oil.

The hydrocarbon-based oil is an oil (non-aqueous compound) that is liquid at room temperature (25° C.).

The term "hydrocarbon-based oil" means an oil formed essentially from, or even consisting of, carbon and hydrogen atoms and optionally oxygen and nitrogen atoms, and not containing silicon or fluorine atoms. It may contain alcohol, ester, ether, carboxylic acid, amine and/or amide groups. Preferably, the hydrocarbon-based oil is solely formed from carbon and hydrogen atoms.

The volatile hydrocarbon-based oil can be chosen from:
hydrocarbon-based oils having from 8 to 16 carbon atoms, and especially:
branched $C_8$-$C_{16}$ alkanes, for instance $C_8$-$C_{16}$ isoalkanes of petroleum origin (also known as isoparaffins), for instance isododecane (also known as 2,2,4,4,6-pentamethylheptane), isodecane, isohexadecane and, for example, the oils sold under the trade name Isopar or Permethyl, linear alkanes, for example such as n-dodecane ($C_{12}$) and n-tetradecane ($C_{14}$) sold by Sasol under the references, respectively, Parafol 12-97 and Parafol 14-97, and also mixtures thereof, the undecane-tridecane mixture, mixtures of n-undecane ($C_{11}$) and of n-tridecane ($C_{13}$) obtained in examples 1 and 2 of application WO2008/155059 from the company Cognis, and mixtures thereof, short-chain esters (having from 3 to 8 carbon atoms in total), such as ethyl acetate, methyl acetate, propyl acetate or n-butyl acetate; and mixtures thereof.

More particularly, the content of volatile hydrocarbon-based oil(s) ranges from 20% to 70% by weight and preferably from 30% to 70% by weight relative to the total weight of the composition.

This hydrocarbon-based oil may be provided totally or partly with surface-stabilized polymer particles, in particular when these particles are introduced into the composition in the form of a pre-prepared dispersion of stabilized polymer particles. In this case, the hydrocarbon-based oil present in the composition represents at least the non-aqueous medium of the dispersion of polymer particles.

Advantageously, the hydrocarbon-based oil is apolar (thus formed solely from carbon and hydrogen atoms). The hydrocarbon-based oil is preferably chosen from hydrocarbon-based oils having from 8 to 16 carbon atoms and better still from 12 to 16 carbon atoms, in particular the apolar oils described previously.

Preferentially, the hydrocarbon-based oil is isododecane.

More particularly, the isododecane content ranges from 20% to 70% by weight, preferably from 25% to 70% by weight and even more preferentially from 30% to 70% by weight, relative to the total weight of the composition.

Preferably, the hydrocarbon-based oil(s), in particular isododecane, constitute the only oil(s) of the composition, or is(are) present in a predominant weight content relative to the additional oil(s) that may be present in the composition.

Thus, according to a particular embodiment, the hydrocarbon-based oil(s) is(are) present in a composition of the process according to the invention in a content ranging from 20% to 70% by weight, preferably from 25% to 70% by weight and even more preferentially from 30% to 70% by weight relative to the total weight of the composition, the hydrocarbon-based oil(s) preferably being apolar, more preferentially volatile, even more preferentially having from 8 to 16 carbon atoms, or even better still isododecane.

In accordance with a particular embodiment of the invention, if the composition contains one or more non-volatile oils, their content advantageously does not exceed 10% by weight, preferably does not exceed 5% by weight relative to the total weight of the composition, and better still less than 2% by weight relative to the total weight of the composition, or even is free of non-volatile oil(s).

Polymer Particles

The composition of the process according to the invention moreover comprises particles, which are generally spherical, of at least one surface-stabilized polymer.

Preferably, the particles are introduced into the composition in the form of a dispersion of particles, which are generally spherical, of at least one surface-stabilized polymer, in an oily medium, advantageously containing at least one hydrocarbon-based oil, as defined previously. Therefore, the dispersion is preferably prepared separately before it is introduced into the composition.

The polymer of the particles is a $C_1$-$C_4$ alkyl (meth)acrylate polymer.

The $C_1$-$C_4$ alkyl (meth)acrylate monomers may be chosen from methyl (meth)acrylate, ethyl (meth)acrylate, n-propyl (meth)acrylate, isopropyl (meth)acrylate, n-butyl (meth) acrylate and tert-butyl (meth)acrylate.

A $C_1$-$C_4$ alkyl acrylate monomer is advantageously used.

Preferentially, the polymer of the particles is a methyl acrylate and/or ethyl acrylate polymer.

The polymer of the particles may also comprise an ethylenically unsaturated acid monomer or the anhydride thereof, especially chosen from ethylenically unsaturated acid monomers comprising at least one carboxylic, phosphoric or sulfonic acid function, such as crotonic acid, itaconic acid, fumaric acid, maleic acid, maleic anhydride, styrenesulfonic acid, vinylbenzoic acid, vinylphosphoric acid, acrylic acid, methacrylic acid, acrylamidopropanesulfonic acid or acrylamidoglycolic acid, and salts thereof.

Preferably, the ethylenically unsaturated acid monomer is chosen from (meth)acrylic acid, maleic acid and maleic anhydride.

The salts may be chosen from salts of alkali metals, for example sodium or potassium; salts of alkaline-earth metals, for example calcium, magnesium or strontium; metal salts, for example zinc, aluminum, manganese or copper; ammonium salts of formula $NH_4^+$; quaternary ammonium salts; salts of organic amines, for instance salts of methylamine, dimethylamine, trimethylamine, triethylamine, ethylamine, 2-hydroxyethylamine, bis(2-hydroxyethyl)amine or tris(2-hydroxyethyl)amine; lysine or arginine salts.

The polymer of the particles may thus comprise or consist essentially of from 80% to 100% by weight of $C_1$-$C_4$ alkyl (meth)acrylate and from 0% to 20% by weight of ethylenically unsaturated acid monomer, relative to the total weight of the polymer. According to a first embodiment of the invention, the polymer essentially consists of a polymer of one or more $C_1$-$C_4$ alkyl (meth)acrylate monomers.

According to a second embodiment of the invention, the polymer essentially consists of a copolymer of $C_1$-$C_4$ (meth) acrylate and of (meth)acrylic acid or maleic anhydride.

The polymer of the particles may be chosen from:
methyl acrylate homopolymers,
ethyl acrylate homopolymers,
methyl acrylate/ethyl acrylate copolymers,
methyl acrylate/ethyl acrylate/acrylic acid copolymers,
methyl acrylate/ethyl acrylate/maleic anhydride copolymers,
methyl acrylate/acrylic acid copolymers,
ethyl acrylate/acrylic acid copolymers,
methyl acrylate/maleic anhydride copolymers
ethyl acrylate/maleic anhydride copolymers.

The polymer(s) of the particles preferably comprise(s) from 80% to 100% by weight of $C_1$-$C_4$ alkyl (meth)acrylate and from 0% to 20% by weight of ethylenically unsaturated acid monomer, relative to the total weight of the polymer, the polymer(s) of the particles being chosen from:
methyl acrylate homopolymers,
ethyl acrylate homopolymers,
methyl acrylate/ethyl acrylate copolymers,
methyl acrylate/ethyl acrylate/acrylic acid copolymers,
methyl acrylate/ethyl acrylate/maleic anhydride copolymers,
methyl acrylate/acrylic acid copolymers,
ethyl acrylate/acrylic acid copolymers,
methyl acrylate/maleic anhydride copolymers
ethyl acrylate/maleic anhydride copolymers.

Advantageously, the polymer of the particles is a non-crosslinked polymer.

The polymer of the particles preferably has a number-average molecular weight ranging from 2000 to 10 000 000 and preferably ranging from 150 000 to 500 000.

In the case of a particle dispersion, the polymer(s) of the particles may be present in the dispersion in a content ranging from 21% to 58.5% by weight and preferably ranging from 36% to 42% by weight, relative to the total weight of the dispersion.

The stabilizer is an isobornyl (meth)acrylate polymer chosen from isobornyl (meth)acrylate homopolymer and statistical copolymers of isobornyl (meth)acrylate and of $C_1$-$C_4$ alkyl (meth)acrylate present in an isobornyl (meth) acrylate/$C_1$-$C_4$ alkyl (meth)acrylate weight ratio of greater than 4, preferably greater than 4.5 and even more advantageously greater than or equal to 5. Advantageously, said weight ratio ranges from 4.5 to 19, preferably from 5 to 19 and more particularly from 5 to 12.

Thus, according to a particular embodiment, a composition according to the invention comprises one or more stabilizers, said stabilizer(s) being a statistical copolymer of isobornyl (meth)acrylate and of $C_1$-$C_4$ alkyl (meth)acrylate present in an isobornyl (meth)acrylate/$C_1$-$C_4$ alkyl (meth) acrylate weight ratio of greater than or equal to 5.

Advantageously, the stabilizer is chosen from:
isobornyl acrylate homopolymers,
statistical copolymers of isobornyl acrylate/methyl acrylate,
statistical copolymers of isobornyl acrylate/methyl acrylate/ethyl acrylate,
statistical copolymers of isobornyl methacrylate/methyl acrylate,
in the weight ratio described previously.

The stabilizing polymer preferably has a number-average molecular weight ranging from 10 000 to 400 000 and preferably ranging from 20 000 to 200 000.

The stabilizer is in contact with the surface of the polymer particles and thus makes it possible to stabilize these particles at the surface, in particular in order to keep these particles in dispersion in the non-aqueous medium of the dispersion.

Advantageously, the combination of the stabilizer(s)+polymer(s) of the particles present in particular in the dispersion comprises from 10% to 50% by weight of polymerized isobornyl (meth)acrylate and from 50% to 90% by weight of polymerized $C_1$-$C_4$ alkyl (meth)acrylate, relative to the total weight of the combination of the stabilizer(s)+polymer(s) of the particles.

Preferentially, the combination of the stabilizer(s)+polymer(s) of the particles present in particular in the dispersion comprises from 15% to 30% by weight of polymerized isobornyl (meth)acrylate and from 70% to 85% by weight of polymerized $C_1$-$C_4$ alkyl (meth)acrylate, relative to the total weight of the combination of the stabilizer(s)+polymer(s) of the particles.

Preferably, the stabilizer(s) is(are) soluble in the hydrocarbon-based oil(s), in particular soluble in isododecane.

According to a theory which should not limit the scope of the present invention, the inventors put forward the hypothesis that the surface stabilization of the $C_1$-$C_4$ alkyl (meth) acrylate polymer particles results from a phenomenon of surface adsorption of the stabilizer onto the $C_1$-$C_4$ alkyl (meth)acrylate polymer particles.

When the polymer particles are provided in the composition in the form of a pre-prepared dispersion, the oily medium of this polymer dispersion comprises a first hydrocarbon-based oil. Reference may be made to that which has been indicated previously concerning this oil as regards its nature.

Advantageously, the hydrocarbon-based oil is apolar and preferably chosen from hydrocarbon-based oils having from 8 to 16 carbon atoms, in particular the apolar oils described previously.

Preferentially, the hydrocarbon-based oil is isododecane.

The polymer particles, in particular in the dispersion, preferably have an average size, especially a number-average size, ranging from 50 to 500 nm, especially ranging from 75 to 400 nm and better still ranging from 100 to 250 nm.

In general, a dispersion of polymer particles that is suitable for the invention may be prepared in the following manner, which is given as an example.

The polymerization may be performed in dispersion, i.e. by precipitation of the polymer being formed, with protection of the formed particles with a stabilizer.

In a first step, the stabilizing polymer is prepared by mixing the constituent monomer(s) of the stabilizing polymer with a free-radical initiator, in a solvent known as the synthesis solvent, and by polymerizing these monomers. In a second step, the constituent monomer(s) of the polymer of the particles are added to the stabilizing polymer formed and polymerization of these added monomers is performed in the presence of the radical initiator.

When the non-aqueous medium is a non-volatile hydrocarbon-based oil, the polymerization may be performed in an apolar organic solvent (synthesis solvent), followed by adding the non-volatile hydrocarbon-based oil (which should be miscible with said synthesis solvent) and selectively distilling off the synthesis solvent.

A synthesis solvent which is such that the monomers of the stabilizing polymer and the radical initiator are soluble therein, and the polymer particles obtained are insoluble therein, so that they precipitate therein during their formation, is thus chosen.

In particular, the synthesis solvent may be chosen from alkanes such as heptane or cyclohexane.

When the non-aqueous medium is a volatile hydrocarbon-based oil, the polymerization may be performed directly in said oil, which thus also acts as synthesis solvent. The monomers should also be soluble therein, as should the free-radical initiator, and the polymer of the particles which is obtained should be insoluble therein.

The monomers are preferably present in the synthesis solvent, before polymerization, in a proportion of 5%-20% by weight. The total amount of the monomers may be present in the solvent before the start of the reaction, or part of the monomers may be added gradually as the polymerization reaction proceeds.

The radical initiator may especially be azobisisobutyronitrile or tert-butyl peroxy-2-ethylhexanoate.

The polymerization may be performed at a temperature ranging from 70° C. to 110° C.

The polymer particles are surface-stabilized, when they are formed during the polymerization, by means of the stabilizer.

The stabilization may be performed by any known means, and in particular by direct addition of the stabilizer, during the polymerization.

The stabilizer is preferably also present in the mixture before polymerization of the monomers of the polymer of the particles. However, it is also possible to add it continuously, especially when the monomers of the polymer of the particles are also added continuously.

From 10% to 30% by weight and preferably from 15% to 25% by weight of stabilizer may be used relative to the total weight of monomers used (stabilizer+polymer of the particles).

The dispersion of polymer particles advantageously comprises from 30% to 65% by weight and preferably from 40% to 60% by weight of solids, relative to the total weight of the dispersion.

A composition of the process according to the invention may thus comprise from 3% to 40% by weight and more preferentially from 4% to 35% by weight of polymer particles as described previously, relative to the total weight of the composition (content expressed as solids).

Colorants

The compositions employed in the processes in accordance with the invention may comprise at least one colorant.

This (or these) colorant(s) is(are) preferably chosen from pulverulent substances, liposoluble dyes and water-soluble dyes, and mixtures thereof.

Preferably, the compositions according to the invention comprise at least one pulverulent colorant. The pulverulent colorants may be chosen from pigments and nacres, and preferably from pigments.

The pigments may be white or colored, mineral and/or organic, and coated or uncoated. Among the mineral pigments, mention may be made of metal oxides, in particular titanium dioxide, optionally surface-treated, zirconium, zinc or cerium oxides, and also iron, titanium or chromium oxides, manganese violet, ultramarine blue, chromium hydrate and ferric blue. Among the organic pigments that may be mentioned are carbon black, pigments of D & C type and lakes based on cochineal carmine or on barium, strontium, calcium or aluminum.

The nacres may be chosen from white nacreous pigments such as mica coated with titanium or with bismuth oxychloride, colored nacreous pigments such as titanium mica with iron oxides, titanium mica with in particular ferric blue or chromium oxide, titanium mica with an organic pigment of the abovementioned type, and also nacreous pigments based on bismuth oxychloride.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto.

Preferably, the pigments contained in the compositions according to the invention are chosen from metal oxides. More preferentially, the pigments contained in the compositions according to the invention are chosen from iron oxides, such as especially those sold under the name Sunpuro Black Iron Oxide C33-7001® by the company Sun.

Thus, according to a particular embodiment, a composition according to the invention also comprises at least one colorant, the colorant(s) preferably being chosen from pulverulent materials, in particular pigments, more particularly from metal oxides such as iron oxides.

According to a particular embodiment, a composition of the process according to the invention may comprise organic pigments, for example carbon black particles.

Thus, according to a preferred embodiment, the composition of the process according to the invention comprises carbon black particles as pigments.

The colorants may be present in a content ranging from 0.01% to 30% by weight relative to the total weight of the composition and in particular from 1% to 22% by weight relative to the total weight of the composition.

Preferably, the colorant(s) are chosen from one or more metal oxides that are present in a content of greater than or equal to 1% by weight relative to the total weight of the composition, and advantageously inclusively between 3% and 22% by weight relative to the total weight of the composition.

According to one preferred embodiment, the composition of the process according to the invention is free of colorant.

Additives

The compositions employed in a process according to the invention may also comprise any cosmetic active agent, such as active agents chosen from an additional volatile or non-volatile silicone oil, fibers, fillers, antioxidants, preserving agents, fragrances, bactericidal active agents, neutralizers, emollients, moisturizers, trace elements, softeners, sequestrants, acidifying or basifying agents, hydrophilic or lipophilic active agents, coalescers, vitamins, thickeners, and mixtures thereof.

It is a matter of routine operation for those skilled in the art to adjust the nature and the amount of the additives present in the compositions employed in a process in accordance with the invention such that the desired cosmetic properties thereof are not thereby affected.

The composition preferably comprises less than 5% by weight of water, better still less than 2% by weight of water, or even less than 1% by weight of water relative to the total weight of the composition, and is especially free of water.

According to a preferred embodiment, a composition of the process according to the invention is in the form of a product for the eyelashes.

According to another embodiment, a composition of the process of the invention may advantageously be in the form of a product for the eyebrows.

A composition according to the invention is preferably in the form of a composition for making up keratin fibers, in particular the eyelashes.

Such compositions are especially prepared according to the general knowledge of those skilled in the art.

Throughout the description, including the claims, the term "comprising a" should be understood as being synonymous with "comprising at least one", unless otherwise specified.

The terms "between . . . and . . . " and "ranging from . . . to . . . " should be understood as being inclusive of the limits, unless otherwise specified.

In the description and the examples, the percentages are percentages by weight, unless otherwise indicated. The percentages are thus given by weight relative to the total weight of the composition. The ingredients are mixed in the order and under the conditions that are easily determined by those skilled in the art.

I. EXAMPLES OF PREPARATION OF DISPERSIONS

Example 1

In a first step, 1300 g of isododecane, 337 g of isobornyl acrylate, 28 g of methyl acrylate and 3.64 g of tert-butyl peroxy-2-ethylhexanoate (Trigonox 21S from Akzo) were placed in a reactor. The isobornyl acrylate/methyl acrylate mass ratio is 92/8. The mixture was heated to 90° C. under argon with stirring.

After 2 hours of reaction, 1430 g of isododecane were added to the reactor feedstock and the mixture was heated to 90° C.

In a second step, a mixture of 1376 g of methyl acrylate, 1376 g of isododecane and 13.75 g of Trigonox 21S were run in over 2 hours 30 minutes, and the mixture was left to react for 7 hours. 3.3 liters of isododecane were then added and part of the isododecane was evaporated off to obtain a solids content of 50% by weight.

A dispersion of methyl acrylate particles stabilized with a statistical copolymer stabilizer containing 92% isobornyl acrylate and 8% methyl acrylate in isododecane was obtained.

The oily dispersion contains in total (stabilizer+particles) 80% methyl acrylate and 20% isobornyl acrylate.

The polymer particles of the dispersion have a number-average size of about 160 nm.

The dispersion is stable after storage for 7 days at room temperature (25° C.).

Example 2

A dispersion of polymer in isododecane was prepared according to the preparation method of example 1, using:

Step 1: 275.5 g of isobornyl acrylate, 11.6 g of methyl acrylate, 11.6 g of ethyl acrylate, 2.99 g of Trigonox 21, 750 g of isododecane; followed by addition, after reaction, of 750 g of isododecane.

Step 2: 539.5 g of methyl acrylate, 539.5 g of ethyl acrylate, 10.8 g of Trigonox 21S, 1079 g of isododecane. After reaction, addition of 2 liters of isododecane and evaporation to obtain a solids content of 35% by weight.

A dispersion in isododecane of methyl acrylate/ethyl acrylate (50/50) copolymer particles stabilized with an isobornyl acrylate/methyl acrylate/ethyl acrylate (92/4/4) statistical copolymer stabilizer was obtained.

The oily dispersion contains in total (stabilizer+particles) 40% methyl acrylate, 40% ethyl acrylate and 20% isobornyl acrylate.

The dispersion is stable after storage for 7 days at room temperature (25° C.).

Example 3

A dispersion of polymer in isododecane was prepared according to the preparation method of example 1, using:

Step 1: 315.2 g of isobornyl acrylate, 12.5 g of methyl acrylate, 12.5 g of ethyl acrylate, 3.4 g of Trigonox 21, 540 g of isododecane, 360 g of ethyl acetate; followed by addition, after reaction, of 540 g of isododecane and 360 g of ethyl acetate.

Step 2: 303 g of methyl acrylate, 776 g of ethyl acrylate, 157 g of acrylic acid, 11 g of Trigonox 21S, 741.6 g of isododecane and 494.4 g of ethyl acetate. After reaction, addition of 3 liters of an isododecane/ethyl acetate mixture (60/40 weight/weight) and total evaporation of the ethyl acetate and partial evaporation of the isododecane to obtain a solids content of 44% by weight.

A dispersion in isododecane of methyl acrylate/ethyl acrylate/acrylic acid (24.5/62.8/12.7) copolymer particles stabilized with an isobornyl acrylate/methyl acrylate/ethyl acrylate (92/4/4) statistical copolymer stabilizer was obtained.

The oily dispersion contains in total (stabilizer+particles) 10% acrylic acid, 20% methyl acrylate, 50% ethyl acrylate and 20% isobornyl acrylate.

The dispersion is stable after storage for 7 days at room temperature (25° C.).

Example 4

A dispersion of polymer in isododecane was prepared according to the preparation method of example 1, using:

Step 1: 315.2 g of isobornyl acrylate, 12.5 g of methyl acrylate, 12.5 g of ethyl acrylate, 3.4 g of Trigonox 21, 540 g of isododecane, 360 g of ethyl acetate; followed by addition, after reaction, of 540 g of isododecane and 360 g of ethyl acetate.

Step 2: 145 g of methyl acrylate, 934 g of ethyl acrylate, 157 g of acrylic acid, 12.36 g of Trigonox 21S, 741.6 g of isododecane and 494.4 g of ethyl acetate. After reaction, addition of 3 liters of an isododecane/ethyl acetate mixture (60/40 weight/weight) and total evaporation of the ethyl acetate and partial evaporation of the isododecane to obtain a solids content of 44% by weight.

A dispersion in isododecane of methyl acrylate/ethyl acrylate/acrylic acid (11.7/75.6/12.7) copolymer particles stabilized with an isobornyl acrylate/methyl acrylate/ethyl acrylate (92/4/4) statistical copolymer stabilizer was obtained.

The oily dispersion contains in total (stabilizer+particles) 10% acrylic acid, 10% methyl acrylate, 60% ethyl acrylate and 20% isobornyl acrylate.

The dispersion is stable after storage for 7 days at room temperature (25° C.).

Example 5

A dispersion of polymer in isododecane was prepared according to the preparation method of example 1, using:

Step 1: 48 g of isobornyl acrylate, 2 g of methyl acrylate, 2 g of ethyl acrylate, 0.52 g of Trigonox 21, 57.6 g of isododecane, 38.4 g of ethyl acetate; followed by addition, after reaction, of 540 g of isododecane and 360 g of ethyl acetate.

Step 2: 98 g of methyl acrylate, 73 g of ethyl acrylate, 25 g of maleic anhydride, 1.96 g of Trigonox 21S, 50.4 g of isododecane and 33.60 g of ethyl acetate. After reaction, addition of 1 liter of an isododecane/ethyl acetate mixture (60/40 weight/weight) and total evaporation of the ethyl acetate and partial evaporation of the isododecane to obtain a solids content of 46.2% by weight.

A dispersion in isododecane of methyl acrylate/ethyl acrylate/maleic anhydride (50/37.2/12.8) copolymer particles stabilized with an isobornyl acrylate/methyl acrylate/ ethyl acrylate (92/4/4) statistical copolymer stabilizer was obtained.

The oily dispersion contains in total (stabilizer+particles) 10% maleic anhydride, 30% methyl acrylate, 40% ethyl acrylate and 20% isobornyl acrylate.

The dispersion is stable after storage for 7 days at room temperature (25° C.).

Example 6

A dispersion of polymer in isododecane was prepared according to the preparation method of example 1, using:

Step 1: 48.5 g of isobornyl methacrylate, 4 g of methyl acrylate, 0.52 g of Trigonox 21, 115 g of isododecane; followed by addition, after reaction, of 80 g of isododecane.

Step 2: 190 g of methyl acrylate, 1.9 g of Trigonox 21S, 190 g of isododecane. After reaction, addition of 1 liter of isododecane and partial evaporation of the isododecane to obtain a solids content of 48% by weight.

A dispersion in isododecane of methyl acrylate polymer particles stabilized with an isobornyl methacrylate/methyl acrylate (92/8) statistical copolymer stabilizer was obtained.

The oily dispersion contains in total (stabilizer+particles) 80% methyl acrylate and 20% isobornyl methacrylate.

The dispersion is stable after storage for 7 days at room temperature (25° C.).

II. EXAMPLES OF COMPOSITIONS FOR FIBERS

The following compositions 1 to 6 in accordance with the invention were prepared as described below, in order to be employed in a process in accordance with the invention in order to elongate and/or densify fibers.

The components are mixed, then dispersed under hot conditions at a temperature of 80-85° C., with Rayneri stirring for 1 hour.

|  | (Methyl acrylate)-co-(isobornyl acrylate) (80.7/19.3) copolymer dissolved in isododecane (Oily dispersion according to example 1) | Styrene/ethylene-propylene diblock copolymer (37/63) (Kraton G1701 EU SQR 1111 sold by Kraton Polymer) | Hydrogenated styrene/methylstyrene/indene copolymer (Regalite R1100 CH Hydrocarbon Resin sold by Eastman Chemical) | Isododecane (Isododecane sold by Ineos) |
|---|---|---|---|---|
| Formula 1 according to the invention | 48% | 0% | 8% | 44% |
| Formula 2 according to the invention | 8% | 2% | 24% | 66% |
| Formula 3 according to the invention | 68% | 3% | 28% | 1% |
| Formula 4 according to the invention | 16% | 6% | 32% | 46% |
| Formula 5 according to the invention | 8% | 7% | 52% | 33% |
| Formula 6 according to the invention | 8% | 16% | 8% | 68% |

Measurements Performed and Results

Method for Evaluation Adhesion During Drying:

The adhesion during drying is evaluated at 20° C. by means of the texture analyzer sold under the name TA-TX2i by the company Rheo.

A 30 µl drop of formulation, when pipettable, is deposited on a contrast card (Byko). A flat steel bead then comes into contact with the drop at an approach speed of 5 mm·s$^{-1}$ and a force of 1 N for a contact time of 5 seconds. The bead is then retracted at the same speed of 5 mm·s$^{-1}$. This operation is repeated 50 times.

The adhesion is considered to be sufficiently high when the value is greater than 2.5 N.

Viscosity Measurement

The viscosity of the compositions was measured qualitatively. Thus, it was determined qualitatively whether the composition tested is liquid, viscous or very viscous.

Thus, the consistency of the compositions tested was observed by means of a pipette at room temperature.

| Measurements | Viscosity Qualitative measurement | Adhesion during drying |
| --- | --- | --- |
| Formulation 1 | Liquid | 2.91 |
| Formulation 2 | Liquid | 2.6 |
| Formulation 3 | Viscous | 2.88 |
| Formulation 4 | Very viscous | 2.6 |
| Formulation 5 | Very viscous | 2.9 |
| Formulation 6 | Very viscous | 2.8 |

The compositions according to the invention range from liquid to very viscous, and can therefore be applied to the skin and the fibers.

The measurements of adhesion during drying are very good. They are all greater than 2.5.

Thus, the compositions may be used advantageously in a process according to the invention making it possible to elongate and/or densify the fibers.

The invention claimed is:

1. A method for the elongation and/or densification of fibers, on a keratin material, comprising applying an adhesive cosmetic composition to the fibers and/or to the keratin material;
wherein the composition comprises:
one volatile hydrocarbon-based oil,
particles of at least one polymer that is surface-stabilized with a stabilizer, the polymer of the particles being a $C_1$-$C_4$ alkyl (meth)acrylate polymer; the stabilizer being an isobornyl (meth)acrylate polymer chosen from isobornyl (meth)acrylate homopolymer and statistical copolymers of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than 4; and
a hydrophobic film-forming polymer.

2. The method as claimed in claim 1, wherein said particles are in dispersion in a non-aqueous medium containing at least the volatile hydrocarbon-based oil.

3. The method as claimed in claim 1, wherein the hydrocarbon-based oil(s) is(are) present in the composition in a content ranging from 20% to 70% by weight relative to the total weight of the composition.

4. The method as claimed in claim 1, wherein the particles of the polymer(s) are present in an amount ranging from 3% to 40% by weight relative to the total weight of the composition.

5. The method as claimed in claim 1, wherein the polymer(s) of the particles is(are) one (or more) methyl acrylate and/or ethyl acrylate polymer(s).

6. The method as claimed in claim 1, wherein the polymer(s) of the particles comprise(s) an ethylenically unsaturated acid monomer or the anhydride thereof.

7. The method as claimed in claim 1, wherein the polymer(s) of the particles comprise(s) from 80% to 100% by weight of $C_1$-$C_4$ alkyl (meth)acrylate and from 0% to 20% by weight of ethylenically unsaturated acid monomer, relative to the total weight of the polymer, the polymer(s) of the particles being selected from the group consisting of:
methyl acrylate homopolymers,
ethyl acrylate homopolymers,
methyl acrylate/ethyl acrylate copolymers,
methyl acrylate/ethyl acrylate/acrylic acid copolymers,
methyl acrylate/ethyl acrylate/maleic anhydride copolymers,
methyl acrylate/acrylic acid copolymers,
ethyl acrylate/acrylic acid copolymers,
methyl acrylate/maleic anhydride copolymers and
ethyl acrylate/maleic anhydride copolymers.

8. The method as claimed in claim 1, wherein the stabilizer(s) is(are) a statistical copolymer of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than or equal to 5.

9. The process as claimed in claim 1, wherein the stabilizer(s) is(are) selected from the group consisting of:
isobornyl acrylate homopolymers,
statistical copolymers of isobornyl acrylate/methyl acrylate,
statistical copolymers of isobornyl acrylate/methyl acrylate/ethyl acrylate, and
statistical copolymers of isobornyl methacrylate/methyl acrylate.

10. The method as claimed in claim 1, wherein the combination of the stabilizer(s)+polymer(s) of the particles comprises from 10% to 50% by weight of polymerized isobornyl (meth)acrylate and from 50% to 90% by weight of polymerized $C_1$-$C_4$ alkyl (meth)acrylate, relative to the total weight of the combination of the stabilizer+polymer of the particles.

11. The method as claimed in claim 1, wherein the composition comprises less than 5% by weight of water relative to the total weight of the composition.

12. The method as claimed in claim 1, wherein the hydrophobic film-forming polymer is a hydrocarbon-based diblock copolymer.

13. The method as claimed in claim 1, wherein the hydrophobic film-forming polymer is a hydrocarbon-based block copolymer present in the composition in a content ranging from 0% to 18% by weight relative to the total weight of the composition.

14. The method as claimed in claim 1, wherein the hydrophobic film-forming polymer is a hydrocarbon-based resin selected from the group consisting of indene hydrocarbon-based resins, aliphatic pentadiene resins, mixed resins of pentanediene and of indene, diene resins of cyclopentanediene dimers, diene resins of isoprene dimers and mixtures thereof.

15. The method as claimed in claim 1 wherein the hydrophobic film-forming polymer is a hydrocarbon-based resin(s) present in a content ranging from 0% to 70% by weight relative to the total weight of the composition.

16. The method as claimed in claim 1, wherein the composition further comprises a styrene-ethylene/propylene diblock copolymer and an indene hydrocarbon-based resin.

17. The method as claimed in claim 1, wherein the composition further comprises at least one colorant.

* * * * *